(12) United States Patent
Zhou et al.

(10) Patent No.: US 10,017,436 B1
(45) Date of Patent: Jul. 10, 2018

(54) METHOD OF MAKING 1,1,1,2,3-PENTACHLOROPROPANE

(71) Applicant: Jiangxi Tianyu Chemical Co., Ltd., Ji'an (CN)

(72) Inventors: Zhong Zhou, Ji'an (CN); Haipeng Xu, Ji'an (CN); Yiming Yu, Ji'an (CN); Peng Peng, Ji'an (CN); Yaling Zhao, Ji'an (CN); Xichao Wang, Ji'an (CN); Xiaori Yue, Shanghai (CN)

(73) Assignee: Jiangxi Tianyu Chemical Co., Ltd., Ji'an (CN)

( * ) Notice: Subject to any disclaimer, the term of this patent is extended or adjusted under 35 U.S.C. 154(b) by 0 days.

(21) Appl. No.: 15/935,085

(22) Filed: Mar. 26, 2018

(30) Foreign Application Priority Data

Nov. 22, 2017 (CN) .......................... 2017 1 1176299

(51) Int. Cl.
*C07C 17/23* (2006.01)
*C07C 17/087* (2006.01)

(52) U.S. Cl.
CPC ............ *C07C 17/23* (2013.01); *C07C 17/087* (2013.01)

(58) Field of Classification Search
CPC .............................. C07C 17/23; C07C 17/087
See application file for complete search history.

(56) References Cited

U.S. PATENT DOCUMENTS

| 4,650,914 A | 3/1987 | Woodard |
| 8,877,991 B2 | 11/2014 | Yang et al. |
| 8,889,927 B2 | 11/2014 | Yang et al. |
| 8,889,928 B2 | 11/2014 | Yang et al. |
| 8,907,147 B2 | 12/2014 | Wang et al. |
| 8,993,816 B2 | 3/2015 | Yang et al. |
| 9,139,495 B2 | 9/2015 | Wilson et al. |
| 2012/0289751 A1* | 11/2012 | Nose ...................... C07C 17/25 570/226 |

* cited by examiner

*Primary Examiner* — Jafar F Parsa
(74) *Attorney, Agent, or Firm* — Dilworth IP, LLC

(57) ABSTRACT

The present invention provides a method of making 1,1,1,2,3-pentachloropropane comprising: (1) utilizing 1,1,1,3-tetrachloropropane as a raw material and 1,1,1,2,3-pentachloropropane as a solvent to carry out a dehydrochlorination reaction to obtain 1,1,3-trichloropropene, and after the reaction, (2) introducing chlorine gas into the reaction system to carry out a chlorination reaction to obtain 1,1,1,2,3-pentachloropropane. In the present invention, 1,1,1,2,3-pentachloropropane acts as a solvent or a diluent, and may act as an inhibitor to prevent the production of high-boiling residues such as dimers, oligomers or polymers during the dehydrochlorination process. Then, the conversion rate of 1,1,1,3-tetrachloropropane is increased, and consequently, the yield of final product 1,1,1,2,3-pentachloropropane is also increased. The preparation method of the present invention can be used in an batch reaction mode, and can also be used in a continuous reaction process, and is suitable for industrial production, thus having a wide range of possible applications.

19 Claims, 1 Drawing Sheet

METHOD OF MAKING 1,1,1,2,3-PENTACHLOROPROPANE

TECHNICAL FIELD

The present invention belongs to the technical field of chemical synthesis, and relates to a preparation method for the manufacture of 1,1,1,2,3-pentachloropropane.

BACKGROUND

Chlorinated hydrocarbon compounds are often used as raw materials for preparing refrigerants, blowing agents, aerosol propellants, biocides and polymers. 1,1,2,3-tetrachloropropene is one of the main intermediates for preparing triallate, which is a chemical herbicide, and is also the main intermediate for the manufacture of 2,3,3,3-tetrafluoropropene, which is a new environmentally friendly refrigerant. One of the latest technologies for making 1,1,2,3-tetrachloropropene is dehydrochlorination of 1,1,1,2,3-pentachloropropane. One of the methods in the art for preparing 1,1,1,2,3-pentachloropropane is to use carbon tetrachloride and ethylene as raw materials to firstly prepare 1,1,1,3-tetrachloropropane, then conduct a dehydrochlorination to make 1,1,3-trichloropropene, and finally conduct an addition reaction with chlorine gas to prepare 1,1,1,2,3-pentachloropropane. This method of making 1,1,2,3-tetrachloropropene through four steps by using carbon tetrachloride and ethylene as raw materials is described in the following reaction equations:

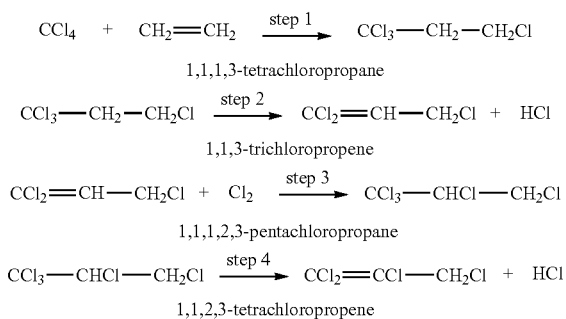

U.S. Pat. No. 4,650,914 discloses a process for preparing 1,1,2,3-tetrachloropropene from carbon tetrachloride and ethylene where a concentrated aqueous solution of sodium hydroxide was used in the dehydrochlorination of 1,1,1,3-tetrachloropropane to prepare 1,1,3-trichloropropene, resulting in a large amount of waste water, and thus the entire process was not environmentally friendly. U.S. Pat. No. 8,907,147 and U.S. Pat. No. 8,993,816 disclose processes for preparing 1,1,2,3-tetrachloropropene where the dehydrochlorination of 1,1,1,3-tetrachloropropane to prepare 1,1,3-trichloropropene, was adopted via continuously charging 1,1,1,3-tetrachloropropane and continuously discharging 1,1,3-trichloropropene with rectification at 120° C. in the presence of ferric chloride, a Lewis acid catalyst. However, the control of polymerization side reactions was very difficult for the processes.

In the current state of the art, there are various side reactions such as polymerization and isomerization in the dehydrochlorination of polychlorinated hydrocarbons when a Lewis acid catalyst, such as anhydrous ferric chloride, is used. In particular, when 1,1,1,3-tetrachloropropane is dehydrochlorinated to make 1,1,3-trichloropropene (i.e. the step 2 in the above reaction sequence), dimerization, oligomerization, and/or polymerization occur extremely easily in the presence of a Lewis acid catalyst due to the presence of 1,1,3-trichloropropene. As a result, the reaction forms a lot of high boiling by-products, including carbonaceous materials such as coke, and turns black, and the catalyst is deactivated. Consequently, the yield of 1,1,1,2,3-pentachloropropane (i.e. the steps 2 and 3 in the above reaction sequence), which is the key intermediate of preparing 1,1,2,3-tetrachloropropene, is decreased, which further results in a decrease in the overall yield in preparing 1,1,2,3-tetrachloropropene.

In the art, in order to reduce the production of high boiling by-products, polymers or tar, U.S. Pat. No. 8,877,991 reduces the generation of high-boiling residues by adding water, however, the addition of water may cause corrosion in the production system. U.S. Pat. No. 8,889,927 reduces the generation of high-boiling residues by using the high-boiling materials produced in the previous step to inhibit the formation of dimers, oligomers and/or polymers. These high boiling materials generated in the previous step can deactivate the catalyst and complicate the reaction and purification system. U.S. Pat. No. 8,889,928 discloses the addition of a stabilizer or antioxidant to inhibit the production of dimers or polymers, however, the addition of a stabilizer or antioxidant increases the cost of production and waste treatment. U.S. Pat. No. 9,139,495 discloses a method which reduces the generation of high-boiling residues by adding carbon tetrachloride, however, carbon tetrachloride may destroy the ozone layer. The Montreal Protocol allows the use of carbon tetrachloride as a raw material but does not allow the use of carbon tetrachloride for other purposes, especially as a solvent or an additive.

Therefore, in the art, in order to increase the yield of 1,1,1,2,3-pentachloropropane and 1,1,2,3-tetrachloropropene, and to reduce the production cost, it is urgent to develop a manufacturing technology which is low-cost, easy to scale up and perform in commercial production, while having high selectivity and yield.

SUMMARY

In view of the deficiencies of the prior art, the object of the present invention is to provide a superior method of making 1,1,1,2,3-pentachloropropane.

The following technical solutions are adopted by the present invention to achieve the purpose of the present invention:

In one embodiment, the present invention provides a method of making 1,1,1,2,3-pentachloropropane comprising the following steps of:

(1) Utilizing 1,1,1,3-tetrachloropropane as a raw material and 1,1,1,2,3-pentachloropropane as a solvent or diluent, and a dehydrochlorination is carried out to obtain 1,1,3-trichloropropene, which is further described in the following reaction equation:

(2) Following the reaction in step (1), chlorine gas is introduced into the reaction system to carry out a chlorination reaction to obtain 1,1,1,2,3-pentachloropropane, which is further described in the following reaction equation:

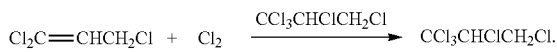

$$Cl_2C=CHCH_2Cl + Cl_2 \xrightarrow{CCl_3CHClCH_2Cl} CCl_3CHClCH_2Cl.$$

In the present invention, 1,1,1,2,3-pentachloropropane does not participate in the dehydrochlorination, whereas it acts as a solvent or a diluent. The production of high-boiling residues (such as dimers, oligomers, or polymers) can be reduced or prevented by adding 1,1,1,2,3-pentachloropropane to the reaction, thus increasing the yield of final product.

In another embodiment, preferably in some cases, chlorine gas is introduced into the reaction system of step (1) to carry out a chlorination reaction after the conversion rate of 1,1,1,3-tetrachloropropane in step (1) reaches 5-100% (for example 5%, 8%, 10%, 15%, 20%, 25%, 30%, 40%, 45%, 50%, 55%, 60%, 70%, 80%, 90% or 100%). Preferably, the chlorination reaction is carried out after the conversion rate is 10-80%, more preferably 15-60%.

The yield of product 1,1,1,2,3-pentachloropropane is increased when the reaction of step (2) is carried out after the conversion rate of 1,1,1,3-tetrachloropropane reaches 5-100%. If the conversion rate of 1,1,1,3-tetrachloropropane in step (1) is less than 5%, the amount of 1,1,3-trichloropropene in the reaction system is relatively low, so that the yield of 1,1,1,2,3-pentachloropropane is low. When the conversion rate of 1,1,1,3-tetrachloropropane in step (1) exceeds 60%, the high-boiling residues produced in the side reactions gradually increase, and the selectivity to generate 1,1,1,2,3-pentachloropropane decreases. In the present invention, chlorine gas is preferably introduced into the reaction system in step (1) to carry out a chlorination reaction after the conversion rate of 1,1,1,3-tetrachloropropane in step (1) reaches 15-60%.

Preferably, the mass percentage of 1,1,1,2,3-pentachloropropane in step (1) is 0-99% excluding 0, i.e., greater than 0 to 99%, preferably 5-80%, more preferably 10-60%, with the mass of the mixture of 1,1,1,3-tetrachloropropane and 1,1,1,2,3-pentachloropropane taken as 100%.

Preferably, the dehydrochlorination in step (1) is carried out in the presence of a catalyst, preferably a Lewis acid catalyst. In the present invention, due to the addition of 1,1,1,2,3-pentachloropropane into the raw materials, side reactions of polymerization do not easily occur in the dehydrochlorination, and the reaction solution does not form carbonaceous materials or coke, and turns black. Furthermore, the catalytic activity of the catalyst is not affected. Therefore, it is easy to control the progress of the reaction so that the yield of final product is increased.

Preferably, the Lewis acid catalyst comprises any one of anhydrous ferric chloride, anhydrous aluminium trichloride, anhydrous zinc chloride or anhydrous ferrous chloride, or a combination of at least two of them.

Preferably, the usage amount of the catalyst is 0.05-1%, for example 0.05%, 0.06%, 0.08%, 0.1%, 0.13%, 0.15%, 0.17%, 0.19%, 0.3%, 0.4%, 0.5%, 0.6%, 0.7%, 0.8%, 0.9% or 1%. Preferably, the usage of catalyst is 0.17% of the mass of 1,1,1,3-tetrachloropropane in step (1).

In the present invention, the catalyst may be added all at one time or in batches during the reaction. Preferably, the catalyst is added all at one time.

Preferably, the dehydrochlorination in step (1) is carried out at a temperature of 50-120° C., for example 50° C., 60° C., 70° C., 80° C., 90° C., 100° C., 110° C. or 120° C. More preferably it is carried out at 60-100° C., even more preferably at 70-90° C.

Preferably, the time of the reaction in step (1) is 0.5-8 hours, for example 0.5 hour, 0.8 hour, 1 hour, 2 hours, 3 hours, 4 hours, 5 hours, 6 hours, 7 hours or 8 hours. More preferably, the time of reaction is 1-6 hours, even more preferably 2-4 hours.

In the present invention, the pressure of the dehydrochlorination reaction in step (1) is not critical. It can be super-atmospheric, atmospheric or under vacuum. Preferably, the dehydrochlorination reaction in step (1) is carried out under ambient pressure.

Preferably, the temperature of the reaction mixture is reduced to room temperature after the conversion rate of 1,1,1,3-tetrachloropropane in step (1) reaches 0-60%, and then chlorine gas is introduced into the reaction system after the reaction of step (1) to carry out a chlorination reaction.

Preferably, the molar ratio of the chlorine gas in step (2) to 1,1,1,3-tetrachloropropane in step (1) is 1-1.5:1, for example 1:1, 1.05:1, 1.1:1, 1.15:1, 1.2:1, 1.25:1, 1.3:1, 1.35:1, 1.4:1, 1.45:1 or 1.5:1. Preferably, the molar ratio is 1.02-1.4:1, more preferably 1.05-1.3:1.

In the present invention, the chlorination reaction in step (2) is a highly exothermic reaction, which needs to be cooled to maintain the temperature at 20-100° C., for example 20° C., 30° C., 40° C., 50° C., 60° C., 70° C., 80° C., 90° C. or 100° C. Preferably, it needs to be cooled 25-90° C., more preferably 30-80° C.

Preferably, the time of the reaction in step (2) is 0.5-8 h, for example 0.5 hour, 0.8 hour, 1 hour, 2 hours, 3 hours, 4 hours, 5 hours, 6 hours, 7 hours or 8 hours. Preferably, the time of reaction is 1-6 hours, more preferably 1.5-4 hours.

In the present invention, the pressure of the chlorination reaction in step (2) is not critical. The reaction may be super-atmospheric, atmospheric or under vacuum. Preferably, the chlorination reaction in step (2) is carried out under ambient pressure.

In the present invention, the chlorination reaction in step (2) requires no catalyst.

In the present invention, 1,1,1,2,3-pentachloropropane acts as a solvent or a diluent, although, without wishing to be bound by theory, it is believed that it can also act as an inhibitor during the dehydrochlorination to prevent the production of high-boiling residues such as dimers, oligomers or polymers. Ultimately, the yield of the final product is increased. After the reaction, the unreacted raw material 1,1,1,3-tetrachloropropane can be recycled by a downstream purification step and the 1,1,1,2,3-pentachloropropane raw material acting as an additive or a diluent can be recycled and returned to the reactor, with little or no loss.

Preferably, the reactions of step (1) and step (2) are carried out in different tank reactors. The reactions of step (1) and step (2) can also be carried out in the same tank reactor and completed via a one-reactor process.

In another embodiment, preferably in some cases, the preparation method of the present invention is a batch reaction process or a continuous reaction process.

Preferably, the batch reaction process is that the reactions in step (1) and step (2) occur sequentially or simultaneously in the same batch tank reactor.

Preferably, the continuous reaction process is that the reactions in step (1) and step (2) occur in two continuous stirred tank reactors connected in series or in the same continuous stirred tank reactor.

Preferably, the continuous reaction process is that the reactions in step (1) and step (2) occur simultaneously in the same continuous stirred tank reactor.

In the present invention, 1,1,1,2,3-pentachloropropane prepared by the method can be used for the preparation of 1,1,2,3-tetrachloropropene. Since 1,1,1,2,3-pentachloropropane has a good yield, the preparation of 1,1,2,3-tetrachloropropene from it has a good yield as well.

Compared with the prior art, the present invention has the following beneficial effects: According to the present invention, 1,1,1,2,3-pentachloropropane is prepared by using 1,1,1,3-tetrachloropropane as a raw material and 1,1,1,2,3-pentachloropropane as a solvent or a diluent. In the present invention, 1,1,1,2,3-pentachloropropane acts as a solvent or a diluent, and may also act as an inhibitor to prevent the production of high-boiling residues such as dimers, oligomers or polymers during the dehydrochlorination process. Ultimately, the conversion rate of 1,1,1,3-tetrachloropropane is increased, and thus, the yield of final product 1,1,1,2,3-pentachloropropane is increased, too. In the present invention, the conversion rate of 1,1,1,3-tetrachloropropane can reach 85% or more, or even more than 90%. The preparation method of the present invention can be used in a batch reaction process, and can also be used in a continuous reaction process. It is suitable for industrial production, and thus has a wide range of possible applications.

DETAILED DESCRIPTION

The technical solutions of the present invention are further described below by using specific examples. It should be understood by those skilled in the art that the examples are merely to help understand the present invention and should not be construed as a limitation to the present invention.

All the conversion rates and yields in the following examples are molar conversion rates and yields unless otherwise specified.

Example 1

In this example, 1,1,1,2,3-pentachloropropane was prepared by a batch reaction, with reaction equations as following:

Reaction I:

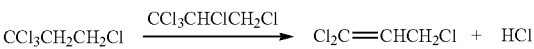

Reaction II:

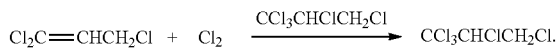

Figure 1:
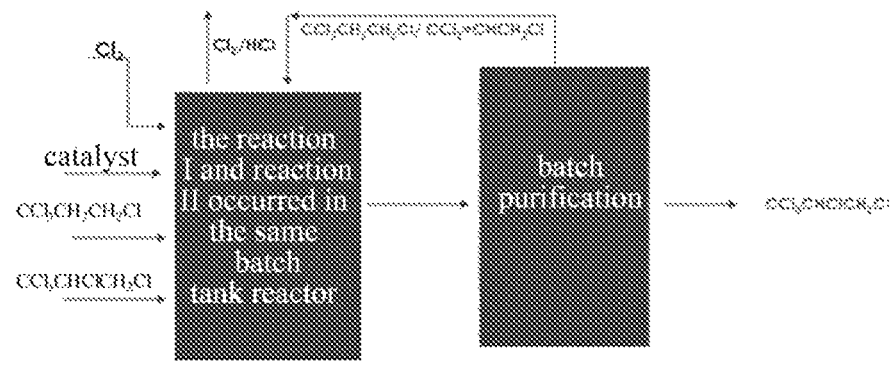
FIG. 1 is a schematic flowchart showing the process for preparing 1,1,1,2,3-pentachloropropane by utilizing a batch process according to the present invention.

As shown in FIG. 1, the reaction I and reaction II of the present invention occurred sequentially in the same batch tank reactor. The reactions of the two steps were carried out in the same 20 L jacketed batch tank reactor. The batch tank reactor was equipped with mechanical agitator. A condenser was installed on the top of the reactor and a tail pipe was connected to the top of the condenser. Acid tail gas was evacuated after absorption by liquid caustic soda having a concentration of 15 wt %.

Reaction I: dehydrochlorination of 1,1,1,3-tetrachloropropane to generate 1,1,3-trichloropropene.

16.8 kg of 1,1,1,3-tetrachloropropane, 4.5 kg of 1,1,1,2,3-pentachloropropane and 0.021 kg of anhydrous ferric chloride were added sequentially into the reactor. The agitation was started. Hot water flowed through the jacket to heat the reactor and cold salt water (or ethanol) of −20° C. flowed through the condenser. Timing was started when the reaction solution was heated to 80° C. The reaction was performed at 80-90° C. for 2 hours. The conversion rate of 1,1,1,3-tetrachloropropane was 43.1% and the composition (GC area %) of the reaction solution was: 35.2% of 1,1,3-trichloropropene, 45.9% of 1,1,1,3-tetrachloropropane, 18.2% of 1,1,1,2,3-pentachloropropane, 0.1% of 1,1,2,3-tetrachloropropene and 0.6% of other chlorocarbons at the end of the reaction.

Reaction II: chlorination of 1,1,3-trichloropropene to generate 1,1,1,2,3-pentachloropropane.

The above described reactor jacket was switched to cold water of 0-5° C. to cool the reaction solution. Chlorine gas was introduced continuously through a dip tube inserted into the reaction solution when the temperature was reduced to 10° C. The temperature of the reaction solution was controlled at 10-15° C. The flow rate of chlorine gas was about 0.025 kg/min. 2.83 kg of chlorine gas was charged within 2 h. Then the chlorine gas charge was stopped and the reaction solution was continuously stirred at 10-15° C. for 1 hour. The mass of the reaction solution was 22.7 kg and the composition (GC area %) was: 0.1% of 1,1,3-trichloropropene, 45.5% of 1,1,1,3-tetrachloropropane, 53.8% of 1,1,1,2,3-pentachloropropane, 0.1% of 1,1,2,3-tetrachloropropene, 0.01% of 1,1,1,3,3-pentachloropropane and 0.49% of other chlorocarbons when the reaction ended.

The reaction solution of the second step was transferred to a 20 L distiller equipped with a 5×270 cm rectification column at the top. Vacuum distillation was performed and condensation was conducted with chilled saline water of −20° C. 9.8 kg of fraction ① was collected at a reflux ratio of 10:1, the composition (GC area %) of which was: 0.2% of 1,1,3-trichloropropene, 99% of 1,1,1,3-tetrachloropropane, 0.4% of 1,1,1,2,3-pentachloropropane, 0.3% of 1,1,2,3-tetrachloropropene and 0.1% of other chlorocarbons. This fraction was applied (i.e. recycled to reuse) as a raw material (as 4 A) of Reaction I. Then, 12.3 kg of fraction ② was collected at a reflux ratio of 1:1, and the content of 1,1,1,2,3-pentachloropropane (GC area %) was 99.5% or more, with a yield of 91%. 0.3 kg of residue remained in the reboiler, with a loss of 0.3 kg.

Example 2

In this example, 1,1,1,2,3-pentachloropropane was prepared by a batch reaction, with a reaction process described as following equations:

Reaction I:

$$CCl_3CH_2CH_2Cl \xrightarrow{CCl_3CHClCH_2Cl} Cl_2C=CHCH_2Cl + HCl$$

Reaction II:

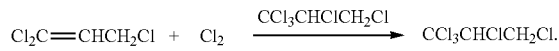
$$Cl_2C=CHCH_2Cl + Cl_2 \xrightarrow{CCl_3CHClCH_2Cl} CCl_3CHClCH_2Cl.$$

As shown in FIG. 1, the reactions of the two steps were carried out in the same 20 L jacketed reactor. The reactor was equipped with mechanical agitator. A condenser was installed on the top of the reactor and a tail pipe was connected to the top of the condenser. Acid tail gas was evacuated after absorption by liquid caustic soda having a concentration of 15 wt %.

Reaction I: dehydrochlorination of 1,1,1,3-tetrachloropropane to generate 1,1,3-trichloropropene.

11.0 kg of 1,1,1,3-tetrachloropropane, 11.0 kg of 1,1,1,2,3-pentachloropropane and 0.033 kg of anhydrous ferric chloride were added sequentially into the reactor. The agitation was started. Hot water flowed through the jacket to heat the reactor and chilled salt water of −20° C. flowed through the condenser. Timing was started when the reaction solution was heated to 70° C. and the temperature was controlled at 70-80° C. for 2.5 hours. The conversion rate of 1,1,1,3-tetrachloropropane was 53.2% and the ° C. composition (GC area %) of the reaction solution was: 28.7% of 1,1,3-trichloropropene, 25.4% of 1,1,1,3-tetrachloropropane, 45.6% of 1,1,1,2,3-pentachloropropane, 0.1% of 1,1,2,3-tetrachloropropene and 0.2% of other chlorocarbons at the end of the reaction.

Reaction II: chlorination of 1,1,3-trichloropropene to generate 1,1,1,2,3-pentachloropropane.

The above described reactor jacket was switched to cold water of 0-5° C. to cool the reaction solution. Chlorine gas was introduced continuously through a dip tube inserted into the reaction solution when the temperature was reduced to 10° C. The temperature of the reaction solution was controlled at 10-15° C. The flow rate of chlorine gas was about 0.025 kg/min. 2.3 kg of chlorine gas was charged within 1.5 h. Then, the chlorine gas charge was stopped and the reaction solution was continuously stirred at 10-15° C. for 1 h. The mass of the reaction solution was 23.1 kg and the composition (GC area %) was: 0.1% of 1,1,3-trichloropropene, 25.0% of 1,1,1,3-tetrachloropropane, 74.6% of 1,1,1,2,3-pentachloropropane, 0.1% of 1,1,2,3-tetrachloropropene, 0.01% of 1,1,1,3,3-pentachloropropane and 0.19% of other chlorocarbons after the reaction.

The reaction solution of the second step was transferred to a 20 L distiller equipped with a 5×270 cm rectification column at the top. Vacuum distillation was performed and condensation was conducted with chilled saline water of −20° C. 5.1 kg of fraction ① was collected at a reflux ratio of 10:1, the composition (GC area %) of which was: 0.3% of 1,1,3-trichloropropene, 98.7% of 1,1,1,3-tetrachloropropane, 0.5% of 1,1,1,2,3-pentachloropropane, 0.4% of 1,1,2,3-tetrachloropropene and 0.1% of other chlorocarbons. This fraction was applied as a raw material (as 4 A) of Reaction I. Then, 17.5 kg of fraction ② was collected at a reflux ratio of 1:1, and the content of 1,1,1,2,3-pentachloropropane (GC area %) was 99.5% or more, with a yield of 93%. 0.2 kg of residue was remained in the reboiler, with a loss of 0.3 kg.

Example 3

In this example, 1,1,1,2,3-pentachloropropane was prepared by a batch reaction, with a reaction process described in the following equations:

Reaction I:

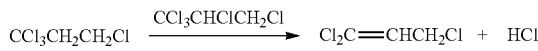
$$CCl_3CH_2CH_2Cl \xrightarrow{CCl_3CHClCH_2Cl} Cl_2C=CHCH_2Cl + HCl$$

Reaction II:

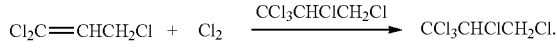
$$Cl_2C=CHCH_2Cl + Cl_2 \xrightarrow{CCl_3CHClCH_2Cl} CCl_3CHClCH_2Cl.$$

A 500 mL jacketed flask was equipped with mechanical agitator. A condenser was installed on the top of the reactor and a tail pipe was connected to the top of the condenser. Acid tail gas was evacuated after absorption by liquid caustic soda having a concentration of 15 wt %.

Reaction I: dehydrochlorination of 1,1,1,3-tetrachloropropane to generate 1,1,3-trichloropropene.

100 g of 1,1,1,3-tetrachloropropane, 400 g of 1,1,1,2,3-pentachloropropane and 0.05 g of anhydrous ferric chloride were added sequentially into the reactor. The agitation was started. Hot water flowed through the jacket to heat the reactor and chilled saline water of −15° C. flowed through the condenser. Timing was started when the reaction solution was heated to 70° C. and the second batch of 0.18 g of ferric chloride was added after 2 h, and the temperature was maintained at 70-80° C. for 5-6 h.

The conversion rate of 1,1,1,3-tetrachloropropane was 89.5% and the selectivity was 90.3% at the end of the reaction.

The composition (GC area %) of the reaction solution was: 17.5% of 1,1,3-trichloropropene, 2.3% of 1,1,1,3-tetrachloropropane, 78.2% of 1,1,1,2,3-pentachloropropane, 0.2% of 1,1,2,3-tetrachloropropene and 1.8% of other chlorocarbons.

Reaction II: chlorination of 1,1,3-trichloropropene to generate 1,1,1,2,3-pentachloropropane.

The above-described reactor jacket was switched to circulating water to cool the reaction solution. Chlorine gas was introduced continuously through a dip tube inserted into the reaction solution when the temperature was reduced to 40° C. The temperature of the reaction solution was controlled at 30-40° C. and 35 g of chlorine gas was introduced in 4-5 h.

The conversion rate of 1,1,1,3-tetrachloropropane was 92.17% and the selectivity of the conversion from 1,1,1,3-tetrachloropropane into 1,1,1,2,3-pentachloropropane was 87.37% at the end of the chlorination.

The composition (GC area %) of the reaction solution was: 0.1% of 1,1,3-trichloropropene, 1.7% of 1,1,1,3-tetrachloropropane, 95.6% of 1,1,1,2,3-pentachloropropane, 0.2% of 1,1,2,3-tetrachloropropene, 2.4% of other chlorocarbons.

Example 4

In this example, 1,1,1,2,3-pentachloropropane was prepared by a batch reaction, with a reaction process described in the following equations:

Reaction I:

Reaction II:

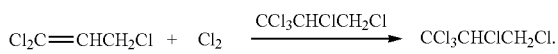

A 500 mL jacketed flask was equipped with mechanical agitator. A condenser was installed on the top of the reactor and a tail pipe was connected to the top of the condenser. Acid tail gas was evacuated after absorption by liquid caustic soda having a concentration of 15 wt %.

Reaction I: dehydrochlorination of 1,1,1,3-tetrachloropropane to generate 1,1,3-trichloropropene. 200 g of 1,1,1,3-tetrachloropropane, 300 g of 1,1,1,2,3-pentachloropropane and 0.5 g of anhydrous ferric chloride were added sequentially into the reactor. The agitation was started. Hot water flowed through the jacket to heat the reactor and chilled saline water of −15° C. flowed through the condenser. Timing was started when the reaction solution was heated to 70° C., and the temperature was maintained at 70-80° C. for 1-2 hours.

The conversion rate of 1,1,1,3-tetrachloropropane was 58.36% and the selectivity of the conversion from 1,1,1,3-tetrachloropropane into 1,1,3-trichloropropene was 95.05% at the end of the reaction.

The composition (GC area %) of the reaction solution was: 24.5% of 1,1,3-trichloropropene, 18.4% of 1,1,1,3-tetrachloropropane, 55.2% of 1,1,1,2,3-pentachloropropane, 0.6% of 1,1,2,3-tetrachloropropene and 1.3% of other chlorocarbons.

Reaction II: chlorination of 1,1,3-trichloropropene to generate 1,1,1,2,3-pentachloropropane. The above-described reactor jacket was switched to cold medium of −5° C. to cool the reaction solution. Chlorine gas was started to be introduced continuously through dip tube inserted into the reaction solution when the temperature was reduced to 0° C. The temperature of the reaction solution was controlled at 0-10° C. and 45 g of chlorine gas was introduced in 2-3 hours.

The conversion rate of 1,1,1,3-tetrachloropropane was 60.27% and the selectivity of the conversion from 1,1,1,3-tetrachloropropane into 1,1,1,2,3-pentachloropropane was 92.74% at the end of the introduction with chlorine gas.

The composition (GC area %) of the reaction solution was: 0.6% of 1,1,3-trichloropropene, 17.6% of 1,1,1,3-tetrachloropropane, 79.6% of 1,1,1,2,3-pentachloropropane, 0.8% of 1,1,2,3-tetrachloropropene and 1.4% of other chlorocarbons after the reaction.

Example 5

Different from Example 4, the reaction of the second step was carried out after the conversion rate of 1,1,1,3-tetrachloropropane in the reaction of the first step reached 35%, consuming 30 g of chlorine gas. Other preparation methods and conditions were the same as those in Example 4. The conversion rate of 1,1,1,3-tetrachloropropane was 37.01% and the selectivity of the conversion from 1,1,1,3-tetrachloropropane to 1,1,1,2,3-pentachloropropane was 98.35% at the end of the reaction of the second step.

Example 6

Different from Example 4, the reaction of the second step was carried out after the conversion rate of 1,1,1,3-tetrachloropropane in the reaction of the first step reached 10%, consuming 9.5 g of chlorine gas. Other preparation methods and conditions were the same as those in Example 4. The conversion rate of 1,1,1,3-tetrachloropropane was 12.56% and the selectivity of the conversion from 1,1,1,3-tetrachloropropane to 1,1,1,2,3-pentachloropropane was 99.40% at the end of the reaction of the second step.

Example 7

The differences with Example 4 were that in the reaction of the first step, anhydrous ferric chloride was replaced by anhydrous aluminum trichloride. Timing was started when the reaction solution was heated to 100° C. The temperature was maintained at 100-120° C. for 0.5 hour.

The conversion rate of 1,1,1,3-tetrachloropropane was 60.90% and the selectivity of the conversion from 1,1,1,3-tetrachloropropane into 1,1,3-trichloropropene was 95.05% at the end of the reaction.

The composition (GC area %) of the reaction solution was: 25.1% of 1,1,3-trichloropropene, 17.3% of 1,1,1,3-tetrachloropropane, 54.7% of 1,1,1,2,3-pentachloropropane, 1.2% 1,1,2,3-tetrachloropropene and 1.7% of other chlorocarbons.

In the reaction of the second step, the temperature of the reaction solution was controlled at 40-50° C., and 71 g of chlorine gas was introduced in 5-6 hours.

The conversion rate of 1,1,1,3-tetrachloropropane was 64.17% and the selectivity of the conversion from 1,1,1,3-tetrachloropropane into 1,1,1,2,3-pentachloropropane was 92.04% at the end of the introduction with chlorine gas.

The composition (GC area %) of the reaction solution was: 0.02% of 1,1,3-trichloropropene, 15.8% of 1,1,1,3-tetrachloropropane, 80.4% of 1,1,1,2,3-pentachloropropane, 0.18% of 1,1,2,3-tetrachloropropene and 3.6% of other chlorocarbons.

Example 8

Figure 2:
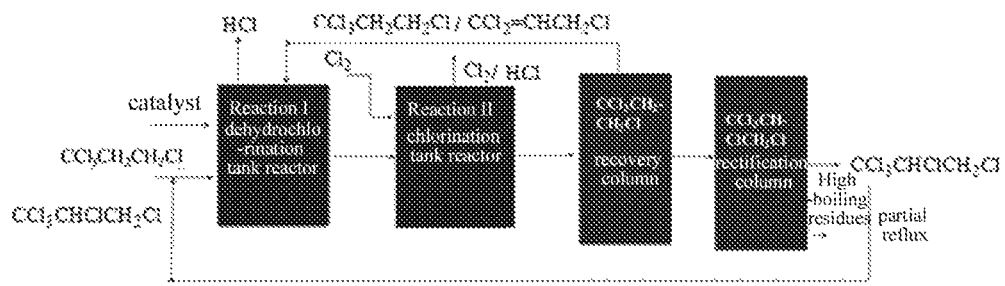
FIG. 2 is a schematic flowchart showing the process for preparing 1,1,1,2,3-pentachloropropane by utilizing two continuous stirred tank reactors (CSTR) connected in series according to the present invention.

In this example, as shown in FIG. 2, two continuous stirred tank reactors (CSTRs) connected in series were utilized to prepare 1,1,1,2,3-pentachloropropane by using 1,1,1,3-tetrachloropropane as a raw material and 1,1,1,2,3-pentachloropropane as a solvent or a diluent. The specific operations were as follows:

The two continuous stirred tank reactors (CSTR) and two distillation columns were connected in series in a pilot plant. The first 20 L continuous stirred tank reactor was equipped with a condenser at the top and the temperature of the condenser was −20° C. 1,1,1,3-tetrachloropropane and 1,1,1,2,3-pentachloropropane were continuously fed at rates of 4.5 kg/h and 3 kg/h, respectively. Anhydrous ferric chloride was periodically added at an average rate of 2.3 g/h. The reactor was heated to 85° C. by steam. A dip tube was inserted into the reactor to about 50% of the reactor content.

The reactor was operated slightly above ambient pressure, 134 KPa, just enough to push the reactor effluent to the next reactor which was located about 0.5 meter lower than the first reactor. The reactor residence time was kept at about 2 hours. About 30% of 1,1,1,3-tetrachloropropane was converted to 1,1,3-trichloropropene in a single pass. The by-product HCl was continuously vented through the condenser and absorbed by a caustic scrubber. The effluent of this reactor was fed to the next CSTR at about 6.6 kg/h rate. The second CSTR was set up the same as the first one. The condenser temperature was maintained at −20° C. The reactor temperature was maintained at about 30° C. The chlorine gas was continuously bubbled into the liquid level at 0.66 kg/h. The reactor effluent was also withdrawn from the reactor through the dip tube, which was inserted at about 50% of reactor level, at about a 7.7 kg/h rate.

The above effluent was fed to a continuous distillation column of 5×270 cm and a reboiler of 40 liters. The distillation column was running under a vacuum of 12 mmHg.

The bottom of the distillation column was fed to the next fractionation column, running under a vacuum of 9-10 mmHg.

Once the steady state was established, the effluent from the second CSTR contained (GC area %): 1.5% of 1,1,3-trichloropropene, 39.5% of 1,1,1,3-tetrachloropropane, 58.3% of 1,1,1,2,3-pentachloropropane, 0.2% of 1,1,2,3-tetrachloropropene, 0.05% of 1,1,1,3,3-pentachloropropane, 0.45% of other chlorocarbons.

The overhead effluent of the distillation column contained (GC area %): 2.6% of 1,1,3-tetrachloropropene and 67.6% of 1,1,1,3-tetrachloropropane and 29.5% 1,1,1,2,3-pentachloropropane, collected at a rate of 4.5 kg/h, which were recycled back to the first reactor.

The purified product of 1,1,1,2,3-pentachloropropane was produced at 3.2 kg/h. 3 kg/h of this final product was recycled back to the first reactor. The bottom stream contains heavies produced at about 0.006 kg/h.

Once the system reached steady state conditions, the fresh feed of 1,1,1,3-tetrachloropropane was reduced to 1.35 kg/h.

The final product stream produced 99.9% of pure 1,1,1,2,3-pentachloropropane at 3.2 kg/h. 1.67 kg/h of the final product was recycled back to the reactor. Along with the recycle of the overhead stream from the first reactor, the total recycle of the 1,1,1,2,3-pentachloropropane was about 3 kg/h (=1.33+1.67 kg/h).

The net production of 1,1,1,2,3-pentachloropropane was 1.53 kg/h. The yield of this process was 96%.

Example 9

Figure 3:
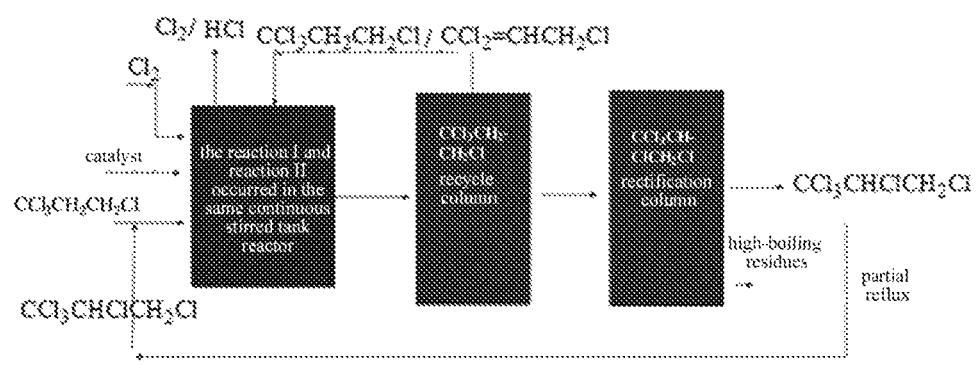
FIG. 3 is a schematic flowchart showing the process for preparing 1,1,1,2,3-pentachloropropane by utilizing one continuous stirred tank reactor (CSTR) according to the present invention.

In this example, as shown in FIG. 3, 1,1,1,2,3-pentachloropropane was prepared in a single continuous stirred tank reactor (CSTR) by utilizing 1,1,1,3-tetrachloropropane as a raw material and 1,1,1,2,3-pentachloropropane as a solvent or a diluent. The specific operations were as following:

In a pilot plant of a single continuous reactor and two rectification columns, 1,1,1,3-tetrachloropropane, 1,1,1,2,3-pentachloropropane and chlorine gas were simultaneously fed into the reactor. The initial charging rates were 3 kg/h, 3 kg/h and 0.6 kg/h, respectively.

The reactor was a 20-liter mechanically-stirred tank reactor, equipped with a condenser sitting on top of it, running at −20° C. Anhydrous ferric chloride was periodically added at an average rate of 2 g/h. The reactor temperature was maintained between 70 and 90° C. A dip tube was inserted to about 50% of the reactor content. The outflow of the reactor was drawn off through the dip tube. The residence time of the reactor was about 3 hours. The HCl generated from the reaction was vented through the condenser to a caustic scrubber along with small amounts of chlorine. The effluent stream from the reactor was fed to a distillation column, running at 12 mmHg pressure and the overhead stream contained the unreacted 1,1,1,3-tetrachloropropane which was recycled back to the reactor. The bottom stream was sent to the next distillation column, running at 9-10 mmHg to fractionate the product 1,1,1,2,3-pentachloropropane. Part of this purified product was recycled back to the reactor to reduce the high boiling materials formation.

After the operation reached steady state, the composition of the effluent from the reactor contained (GC Area %): 2.2% of 1,1,3-trichloropropene, 23.2% of 1,1,1,3-tetrachloropropane, 72.5% of 1,1,1,2,3-pentachloropropane, 1.2% of 1,1,2,3-tetrachloropropene, 0.9% of other chlorocarbons.

After it reached steady state conditions, the fresh feed of 1,1,1,3-tetrachloropropane was reduced to 1.29 kg/h; the 3 kg/h of 1,1,1,2,3-pentachloropropane were all coming from recycles; 2.74 kg/h came from light recycles from the first distillation column; and 0.26 kg/h came from the recycle of the final product. The unreacted intermediate of 1,1,3-trichloropropene and the unreacted 1,1,1,3-tetrchloropropane were also recycled back to the reactor from the overhead stream of the first distillation column. The net production of the final product of 99.9% purity was at about 1.78 kg/h, equivalent to a yield of 86%.

What is claimed is:

1. A method of making 1,1,1,2,3-pentachloropropane comprising the following steps of:
   (1) utilizing 1,1,1,3-tetrachloropropane as a raw material and 1,1,1,2,3-pentachloropropane as a solvent to carry out a dehydrochlorination reaction to obtain 1,1,3-trichloropropene, with the following reaction equation:

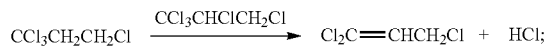

and (2) introducing chlorine gas into the reaction system after the reaction in step (1) to carry out a chlorination reaction to obtain 1,1,1,2,3-pentachloropropane, with the following reaction equation:

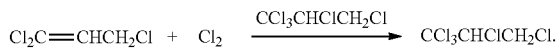

2. The method according to claim 1, wherein chlorine gas is introduced into the reaction system of step (1) to carry out a chlorination reaction after the conversion rate of 1,1,1,3-tetrachloropropane in step (1) reaches 5-100%.

3. The method according to claim 1, wherein the mass percentage content of 1,1,1,2,3-pentachloropropane in step (1) is 0-95% excluding 0, with the mass of the mixture of 1,1,1,3-tetrachloropropane and 1,1,1,2,3-pentachloropropane taken as 100%.

4. The method according to claim 1, wherein the dehydrochlorination reaction in step (1) is carried out in the presence of a catalyst.

5. The method according to claim 4, wherein the catalyst is a Lewis acid catalyst.

6. The method according to claim 5, wherein the Lewis acid catalyst is selected from anhydrous ferric chloride, anhydrous aluminum trichloride, anhydrous zinc chloride, anhydrous ferrous chloride, or mixtures thereof.

7. The method according to claim 4, wherein the usage amount of the catalyst is 0.03-1% based on the mass of 1,1,1,3-tetrachloropropane in step (1).

8. The method according to claim 4, wherein the catalyst is added in at least one portion.

9. The method according to claim 1, wherein the dehydrochlorination reaction in step (1) is carried out at a temperature of 50-120° C.

10. The method according to claim 1, wherein the time of the reaction in step (1) is 0.5-8 hours.

11. The method according to claim 1, wherein the molar ratio of the chlorine gas in step (2) to 1,1,1,3-tetrachloropropane in step (1) is 1-1.5:1.

12. The method according to claim 1, wherein the chlorination reaction in step (2) is carried out at a temperature of 0-100° C.

13. The method according to claim 1, wherein the time of the reaction in step (2) is 0.5-8 h.

14. The method according to claim 1, wherein the reactions of step (1) and step (2) are carried out in different tank reactors or in the same tank reactor and completed through a one-pot process.

15. The method according to claim 1, wherein the preparation method of the present invention is a batch reaction mode or a continuous reaction mode.

16. The method according to claim 15, wherein in the batch reaction process the reactions in step (1) and step (2) occur sequentially or simultaneously in the same batch tank reactor.

17. The method according to claim 15, wherein in the continuous reaction mode the reactions in step (1) and step (2) occur in two continuous stirred tank reactors connected in series.

18. The method according to claim 15, wherein in the continuous reaction mode the reactions in step (1) and step (2) occur simultaneously in the same continuous stirred tank reactor.

19. A process comprising dehydrochlorinating 1,1,1,2,3-pentachloropropane to form 1,1,2,3-tetrachloropropene wherein the 1,1,1,2,3-pentachloropropane was prepared by the method according to claim 1.

* * * * *